(12) United States Patent
Milek et al.

(10) Patent No.: US 9,097,692 B2
(45) Date of Patent: Aug. 4, 2015

(54) METHOD FOR QUANTITATIVELY DETERMINING IMPURITIES IN GLYCERIN

(75) Inventors: Frank Milek, Stuttgart (DE); Rouven Josl, Ostfildern (DE)

(73) Assignee: Aug. Hedinger GmbH & Co. KG, Stuttgart (DE)

( * ) Notice: Subject to any disclaimer, the term of this patent is extended or adjusted under 35 U.S.C. 154(b) by 656 days.

(21) Appl. No.: 13/249,997

(22) Filed: Sep. 30, 2011

(65) Prior Publication Data

US 2012/0083039 A1    Apr. 5, 2012

Related U.S. Application Data

(60) Provisional application No. 61/388,808, filed on Oct. 1, 2010.

(51) Int. Cl.
| | |
|---|---|
| *G01N 33/15* | (2006.01) |
| *G01N 30/06* | (2006.01) |
| *G01N 30/34* | (2006.01) |
| G01N 30/74 | (2006.01) |
| G01N 30/88 | (2006.01) |

(52) U.S. Cl.
CPC ............... *G01N 30/06* (2013.01); *G01N 30/34* (2013.01); *G01N 30/74* (2013.01); *G01N 2030/8872* (2013.01); *Y10T 436/200833* (2015.01); *Y10T 436/202499* (2015.01)

(58) Field of Classification Search
USPC ................................. 436/128, 161, 164, 130
See application file for complete search history.

(56) References Cited

U.S. PATENT DOCUMENTS

| | | | | |
|---|---|---|---|---|
| 5,580,764 | A * | 12/1996 | Holt et al. .................... | 435/118 |
| 6,187,591 | B1 * | 2/2001 | Krepinsky et al. .............. | 436/63 |
| 6,350,902 | B2 * | 2/2002 | Hill et al. ..................... | 560/312 |
| 6,436,311 | B1 * | 8/2002 | Harimoto et al. ........... | 252/181.1 |
| 7,022,674 | B2 * | 4/2006 | DeFelippis et al. ............ | 514/5.9 |
| 7,241,625 | B2 * | 7/2007 | Kitasaka et al. .............. | 436/128 |
| 7,736,612 | B2 * | 6/2010 | Kubota et al. ................ | 423/335 |
| 2003/0207802 | A1 * | 11/2003 | DeFelippis et al. ............. | 514/12 |
| 2004/0248313 | A1 * | 12/2004 | Kitasaka et al. .............. | 436/128 |
| 2006/0175256 | A1 * | 8/2006 | Masten et al. ................ | 210/638 |
| 2006/0275913 | A1 * | 12/2006 | Kitasaka et al. .............. | 436/128 |
| 2008/0033191 | A1 * | 2/2008 | Schoerken et al. ........... | 554/124 |
| 2008/0138481 | A1 * | 6/2008 | Ho et al. ...................... | 426/532 |

FOREIGN PATENT DOCUMENTS

| | | |
|---|---|---|
| EP | 1242121 B1 | 2/2005 |
| EP | 2433651 B1 | 3/2013 |

OTHER PUBLICATIONS

Weisenthal, K. et al, Journal of AOAC International 2000, 83, 859-870.*
Beilin, E. et al, Journal of Pharmaceutical and Biomedical Analysis 2008, 46, 316-321.*
Le Lacheur, R. M. et al, Environmental Science and Technology 1993, 27, 2745-2753.*
Breckenridge, S. M. et al, Journal of Chromatography B 1997, 694, 289-296.*
Wardencki, W. et al, Fresenius' Journal of Analytical Chemistry 2001, 369, 661-665.*
Liu, L.-J. S. et al, Environmental Science and Technology 2001, 35, 2301-2308.*
Biondi, P. A. et al, Chromatographia 2007, 65, 65-68.*
Goncalves et al., "Analysis of aldehydes in beer by gas-diffusion microextraction: Characterization by high-performance liquid chromatography-diode-array detection—atmospheric pressure chemical ionization-mass spectrometry", Journal of Chromatography A, vol. 1217, 2010, pp. 3717-3722.
Cancho et al., "Determination of aldehydes in drinking water using pentafluorobenzylhydroxylamine derivatization and solid-phase microextraction", Journal of Chromatography A, vol. 943, 2001, pp. 1-13.

* cited by examiner

*Primary Examiner* — Arlen Soderquist
(74) *Attorney, Agent, or Firm* — Bacon & Thomas, PLLC

(57) ABSTRACT

The invention relates to a method for quantitatively determining impurities in the form of aldehydes and ketones in glycerin serving for preparing pharmaceuticals, in which the glycerin containing impurities is reacted with a derivatization reagent in a sample solution and the quantity of derivatized impurities is determined. Said method is characterized in that PFBHA, O-(2,3,4,5,6-pentafluorobenzyl)-hydroxylamine hydrochloride, is used as the derivatization reagent, the derivatizing is conducted in the presence of a solubilizer in the form of a polar organic solvent, and liquid chromatographic separation and UV detection are performed. A subject matter of the invention is also the use of glycerin, in which the content of impurities of 9 ppm or less has been determined by means of the described method in a pharmaceutical preparation. According to the invention, impurities in glycerin can be better determined.

12 Claims, No Drawings

METHOD FOR QUANTITATIVELY DETERMINING IMPURITIES IN GLYCERIN

This application claims benefit of U.S. provisional application 61/388,808 filed Oct. 1, 2010 under 35 U.S.C. 119(e).

The invention relates to a method for quantitatively determining impurities in the form of aldehydes and ketones in glycerin serving for the preparation of pharmaceuticals, wherein the glycerin containing the impurities is reacted with a derivatization reagent in a sample solution and the quantity of derivatized impurities is determined.

It is known that pharmaceuticals must fulfil strict quality requirements to be able to be dispensed to the consumer, respectively patient. The ingredients contained in pharmaceuticals and their forms of administration must comply with the recognized pharmaceutical laws which are inter alia defined in pharmacopoeias.

Glycerin is one of those ingredients which are often used in manufacturing pharmaceuticals. Many monographs exist for this chemical substance glycerin in various pharmacopoeias, such as in the European Pharmacopoeia (Ph, Eur.), the American Pharmacopoeia (USP) and the Japanese Pharmacopoeia (JP). Glycerin must comply with the specifications stipulated in these pharmacopoeias.

However, glycerin is susceptible to oxidation. During the preparation as well as storage of glycerin, aldehydes and ketones may develop. The occurrence of such impurities in glycerin can result in quality problems when glycerin is used for preparing pharmaceuticals.

The methods for determining impurities in the form of aldehydes and ketones described in the monographs mentioned above, however, are insufficient. Only the European Pharmacopoeia contains an explicit specification for aldehydes. According to said specification, the aldehyde content is determined by way of derivatizing with pararosaniline chloride and subsequent UV/VIS measurement, with formaldehyde serving as a reference. According to said specification, the aldehyde content must not exceed a maximum of 10 ppm.

In the USP, aldehydes are only detected by the gas-chromatographic test for "related compounds"; the specification limit is in this case at a maximum of 0.1%.

Glycerin may contain aldehydes and ketones in contents up to above 60 ppm and nevertheless fulfil the requirements during the test according to the European Pharmacopoeia. This is due to the fact that the method of the European Pharmacopoeia is imprecise and merely detects formaldehyde while only detecting the other aldehydes and ketones in an insufficient manner. Therefore, there is the risk for the manufacturer of pharmaceuticals that while the ingredient glycerin he has purchased in fact passes the test as per the European Pharmacopoeia, the true content of aldehydes and ketones is not only 10 ppm but far above this value. The manufacturer of pharmaceuticals is thus never aware of this high content of aldehydes and ketones. Due to the reactivity of aldehydes and ketones, however, this can have negative effects on the quality of the finished pharmaceutical.

These problems are also discussed in EP 1 242 121 B1 which provides a summarizing representation of various problems and also a testing method for determining the content of reactive aldehydes in glycerin samples.

This known method is a calorimetric assay in which glyceraldehyde is used as a standard. This known method uses 3-methyl-2-benzothiazolinone-hydrazone-hydrochloride (MBTH). After the reaction has taken place, the absorption of the reaction solution is measured spectrophotometrically at 624 nm.

In this printed publication, this MBTH test is also compared to other known tests. A disadvantage in these known methods is the circumstance that only some of the impurities of glycerin can be detected quantitatively.

The task of the present invention is therefore to provide a method by means of which as many as possible and particular the entirety of impurities in the form of aldehydes and ketones in glycerin can be better determined quantitatively.

This task is solved by a method according to the teaching of the claims.

In the method according to the invention for quantitatively determining aldehydes and ketones, PFBHA is used as a derivatization reagent. Same is O-(2,3,4,5,6-pentafluorobenzyl)-hydroxylamine hydrochloride.

According to the invention, a sample solution containing the glycerin to be tested is mixed with the mentioned derivatization reagent which is preferably present in a buffered aqueous derivatizing solution.

Further, a solubilizer in the form of a polar organic, in particular water-soluble solvent is added. Same can consist, for example, of alcohols having 1 to 5 C atoms, in particular monoalcohols having 1 to 5 C atoms, as well as acetonitrile, with acetonitrile being preferred.

In the method according to the invention, glycerin and the impurities contained therein are reacted with the derivatization reagent in a sample solution.

During this conversion, respectively reaction, the impurities mentioned above are converted into the respective derivatives. The sample solution obtained after the reaction, and consequently the derivatized impurities, are then separated by liquid chromatography.

The derivatizing, respectively converting is preferably conducted in a thermostated space. This space is preferably an autosampler. The derivatizing may be conducted, for example, at a temperature of 0-76° C., preferably 0-60° C., further preferred at 20-35° C., and particularly preferred at about 25° C.

The indicated temperature ranges of 0-76° C. comprise any intermediate, in particular integer temperature values, for instance, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, and 76. The same applies analogously to the preferred temperature ranges of 0° C.-60° C. and 20° C.-35° C.

The concentration of the solubilizer in the sample solution to be tested is preferably 1-80 vol % and particularly preferred about 20 vol %.

Also in these range indications, any of the values falling into said range, and in particular integer values are included and disclosed. Hence, the range of 1-80 vol % includes and discloses at least the following integer single values: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, and 80.

The concentration of glycerin in the sample solution to be tested may be 1-90% mN, preferably 5-50% m/v, and further preferred about 40% m/v. In this case as well, the indicated ranges include any of the values falling within the indicated range, and in particular integer values. Hence, the range for the concentration of glycerin from 5-50% mN includes at least the following integer values: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

The reaction time of the derivatizing conversion, respectively reaction may be 10 minutes-10 days, and is preferably 10-20 hours, e.g. 10, 11, 12, 13, 14, 15, 16, 17, 18, 19 and 20 hours, particularly preferred 15 hours.

The concentration of the derivatization reagent, e.g. PFBHA, in the sample solution is preferably 0.01 mg/ml to 100 mg/ml, particularly preferred 0.2 mg/ml. Also in this case, all of the values within the ranges are included and disclosed, e.g. 0.1, 0.2, 0.3, 0.4, 0.5, 0.6, 0.7, 0.8, 0.9, 1, 2, 3, etc. to 100.

The converting/derivatizing preferably takes place at a pH value from 2 to 7, for example, 2, 3, 4, 5, 6 or 7.

The chromatographic separation (HPLC method) uses a mobile phase consisting of two or more liquids, in particular a mobile phase A which is water or a buffered aqueous phase (preferred), and a mobile phase B which is an organic solvent or solvent mixture.

As buffers, such buffers can be used which are known and usually used in the field of chromatography.

As the organic solvent, a polar protic solvent such as acetic acid, methanol, ethanol, n-propanol or isopropanol, or a polar aprotic solvent such as acetone, acetonitrile, dimethoxyethane, DMF, DMSO, 1,4-dioxane, pyridine or THF may be used. Preferably, acetonitrile is used.

The gradient in the chromatographic separation is selected such that the relative concentrations of the mobile phase, respectively liquids A and B in the first 1 to 100 minutes are between 100% of A: 0% of B and 60% of A: 40% of B and change within 0 and 200 minutes in such a manner that they are between 60% of A: 40% of B and 0% of A: 100% of B.

After the chromatographic separation, a detection of the obtained reaction products takes place, whereby a quantitative determination is performed. This detection preferably is an UV detection.

The UV detection is preferably conducted at a wavelength of 180-400 nm, further preferred at 190-250 nm, and most preferred at about 200 nm. This range as well discloses, respectively includes all of the at least integer values falling into said range. Thus, the range of 190-250 nm includes and discloses at least the following integer values, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, and 250.

By means of the selected chromatographic processing and detecting it is possible to separate the excess of derivatization reagent from the ketone and aldehyde derivatives. Moreover, the ketone and aldehyde derivatives can be separated from each other. This enables a selective determination of each known derivative (for instance, glyceraldehyde (GA), dihydroxyacetone (DHA), hydroxyacetone (HA) and formaldehyde (FA)) and other possible derivatives from oxidation products in the glycerin.

The method according to the invention serves particularly for quantitatively determining glyceraldehyde, dihydroxyacetone, hydroxyacetone and formaldehyde as well as other potential oxidation products in the form of aldehydes and ketones in glycerin. These aldehydes and ketones can of course coexist within the tested glycerin.

The content of the various impurities is preferably calculated by comparing to a derivatized calibrating solution, respectively calibrating sample containing said impurities. In other words, a known solution with exactly defined content of impurities to be determined is treated and derivatized in the same way as a liquid sample, respectively sample solution to be tested.

By means of the method according to the invention it is possible to achieve, at a given matrix of glycerin, a complete reaction of the impurities in the matrix without any components being precipitated. It is moreover possible to attain a complete reaction of the impurities without causing decomposition reactions.

Also a subject matter of the invention is the use of glycerin in which a content of impurities of 9 ppm or less, e.g. 9, 8, 7, 6, 5, 4, 3, 2 and 1 has been determined by means of the method described in the present application for preparing a pharmaceutical, in particular a polypeptide described in EP 1242121 B1, in particular insulin. The term "pharmaceutical" comprises any kind of pharmaceutical composition.

The method according to the invention will be described below in terms of one specific example.

The following reagents are prepared for carrying out the method:

Mobile Phases:
A: 100 μl of 85% phosphoric acid in 1 l of water (1 l for approximately 40 runs)
B: acetonitrile Derivatizing Solution:
0.25 g of PFBHA (O-(2,3,4,5,6-pentafluorobenzyl)-hydroxylamine hydrochloride) is dissolved in 25.0 ml buffer solution, pH=4 (e.g. Certipur citrate/NaOH/HCl, Merck company) in a volumetric flask.

Stock Solution 1 (1000 ppm):
Approximately 95 ml of water is introduced into a 100 ml volumetric flask. About 100 mg of glyceraldehyde and dihydroxyacetone as well as 100 μl each of hydroxyacetone and formaldehyde solution (35%) are admixed. The flask is filled to 100.0 ml with water. The solids are completely dissolved, ultrasound can be used for this purpose.

Stock Solution 2 (10 ppm):
1.0 ml of stock solution 1 is pipetted into a 100 ml volumetric flask and filled to 100.0 ml with water.

Calibration standard Glyc-PFBHA-0.40:
1.0 ml of stock solution 2, 5.0 ml acetonitrile and 0.5 ml derivatizing solution are filled in a 25 ml volumetric flask with water to 25.0 ml.

Calibration standard Glyc-PFBHA-4.00:
10.0 ml of stock solution 2, 5.0 ml acetonitrile and 0.5 ml derivatizing solution are filled in a 25 ml volumetric flask with water to 25.0 ml.

Blank Solution:
5.0 ml of acetonitrile and 0.5 ml derivatizing solution are filled in a 25 ml volumetric flask with water to 25.0 ml.

Sample Solution:
10 g sample, 5.0 ml acetonitrile and 0.5 ml derivatizing solution are filled in a 25 ml volumetric flask with water to 25.0 ml.

Spiked Sample:
10 g sample (glycerin), 5.0 ml of stock solution 2, 5.0 ml acetonitrile and 0.5 ml derivatizing solution are filled in a 25 ml volumetric flask with water to 25.0 ml.

The derivatizing of the various solutions is conducted in an autosampler of a HPLC system at 25° C. The derivatizing is complete when the relative standard deviation of three consecutive measurements of the Glyc-PFBHA-4.00 calibration standard amounts to no more than 2%.

The analytical determination takes place by liquid chromatography with predefinition of the following HPLC conditions:

Column: Discovery C 18, 25 cm×4 mm, 5 μm
Injection volume: 20 μl
Analysis time: 85 min Column temperature: 25° C.
Autosampler temperature: 25° C.
Detector: diode array detector
Wavelength: 200 nm
Gradient: linear ramps

| time (min) | % B |
|---|---|
| 0 | 20 |
| 2 | 20 |
| 60 | 100 |
| 75 | 100 |
| 78 | 20 |

| time (min) | flow (ml/min) |
|---|---|
| 0 | 0.5 |
| 60 | 0.5 |
| 65 | 1.0 |
| 79 | 1.0 |
| 80 | 0.5 |

The order of injections is as follows:

| Solution | Number of injections |
|---|---|
| Glyc-PFBHA-4.0 | until the relative standard deviation of GA, DHA and HA of 3 consecutive measurements is less than 2% (approx. 10 measurements) |
| Blank solution | 1 measurement |
| Glyc-PFBHA-0.4 (calibration) | 1 measurement |
| Glyc-PFBHA-4.0 (calibration) | 1 measurement |
| Spiked sample | 1 measurement |
| Sample | 1 measurement |
| Further samples | x measurements |
| Glyc-PFBHA-4.0 (drift check) | 1 measurement |

Calibration curves are calculated based on the above data. The content of glyceraldehyde, dihydroxyacetone, hydroxyacetone and formaldehyde as well as other possible oxidation products in the sample, respectively samples is calculated on the basis of the calibration curves as ascertained.

This method is validated according to ICH[1] Q2 (R1) (VALIDATION OF ANALYTICAL PROCEDURES: TEXT AND METHODOLOGY).

[1] INTERNATIONAL CONFERENCE ON HARMONISATION OF TECHNICAL REQUIREMENTS FOR REGISTRATION OF PHARMACEUTICALS FOR HUMAN USE.

With the help of the method according to the invention, the impurities and decomposition products contained in glycerin are detected much more precisely than according to the hitherto known methods described in monographs of pharmacopoeia. This increases safety in preparing sensitive pharmaceuticals.

The invention claimed is:

1. A method for quantitatively determining impurities in glycerin serving for preparing pharmaceuticals, wherein the glycerin contains impurities; the impurities are glyceraldehyde, dihydroxyacetone, hydroxyacetone and formaldehyde; and the method comprises the following steps:
   (a) derivatizing the impurities by reacting the glycerine in a buffered aqueous sample solution comprising a derivatization reagent and a polar organic solvent, wherein the buffered aqueous sample solution is at a pH of about between 2 and 7; and the derivatization reagent is O-(2,3,4,5,6-pentafluorobenzyl)-hydroxylamine hydrochloride (PFBHA);
   (b) separating the derivatized impurities of step (a) via high pressure liquid chromatography (HPLC) using a mobile phase A which is water buffered with phosphoric acid and a mobile phase B which is acetonitrile; and
   (c) determining the quantity of the impurities by detecting the separated derivatized impurities of step (b) using ultraviolet (UV) detection at a wavelength of 190 to 250 nm and comparing the results of the UV detection to a standard derivatized calibrating solution containing the impurities.

2. The method of claim 1, wherein the polar organic solvent is acetonitrile.

3. The method of claim 1, wherein the UV detection is conducted at a wavelength of about 200 nm.

4. The method of claim 1, wherein the derivatizing is performed in a thermostated space.

5. The method of claim 4, wherein the derivatizing is performed at 0 to 76° C.

6. The method of claim 5, wherein the derivatizing is performed at about 25° C.

7. The method of claim 1, wherein the concentration of the polar organic solvent in the sample solution is 1 to 80 vol %.

8. The method of claim 7, wherein the concentration of the polar organic solvent in the sample solution is about 20 vol %.

9. The method of claim 1, wherein the concentration of glycerin in the sample solution is 5 to 50% (m/v).

10. The method of claim 9, wherein the concentration of glycerin in the sample solution is about 40% (m/v).

11. The method of claim 1, wherein the reaction time of the derivatization reaction is 10 minutes to 20 hours.

12. The method of claim 1, wherein the HPLC is performed using the following predefined HPLC conditions:
Column: Discovery C 18, 25 cm×4 mm, 5 µm
Injection volume: 20 µl
Analysis time: 85 min
Column temperature: 25° C.
Autosampler temperature: 25° C.
Detector: diode array detector
Wavelength: 200 nm
Gradient: linear ramps

| time (min) | % B |
|---|---|
| 0 | 20 |
| 2 | 20 |
| 60 | 100 |
| 75 | 100 |
| 78 | 20 |

| time (min) | flow (ml/min) |
|---|---|
| 0 | 0.5 |
| 60 | 0.5 |
| 65 | 1.0 |
| 79 | 1.0 |
| 80 | 0.5 |

* * * * *